US006533724B2

(12) United States Patent
McNair (10) Patent No.: US 6,533,724 B2
(45) Date of Patent: Mar. 18, 2003

(54) DECISION ANALYSIS SYSTEM AND METHOD FOR EVALUATING PATIENT CANDIDACY FOR A THERAPEUTIC PROCEDURE

(75) Inventor: Douglas S. McNair, Gloucester, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 09/843,243

(22) Filed: Apr. 26, 2001

(65) Prior Publication Data
US 2002/0193667 A1 Dec. 19, 2002

(51) Int. Cl.[7] .............................................. A61B 5/00
(52) U.S. Cl. ....................................... 600/300; 128/898
(58) Field of Search .......................... 600/300; 128/898, 128/897; 702/181

(56) References Cited

U.S. PATENT DOCUMENTS 5,550,021 A    8/1996    Blum et al.
5,850,339 A    12/1998    Giles
6,193,654 B1 *   2/2001    Richardson et al. ........ 600/300

OTHER PUBLICATIONS

Aaronson, K.D., et al., "Development and Prospective Validation of a Clinical Index to Predict Survival in Ambulatory Patients Referred for Cardiac Transplant Evaluation" *Circulation*, 95:2660–2667 (1997).
Berger, M.M., et al., "Evaluation of the Consistency of Acute Physiology and Chronic Health Evaluation (APACHE II) Scoring in a Surgical Intensive Care Unit" *Crit. Care Med.*, vol. 20, No. 12:1681–1687 (Dec., 1992).
Cady, L.D., et al., "Quantitation of Severity of Critical Illness with Special Reference to Blood Lactate" *Crit. Care Med.*, vol. 1, No. 2:75–79 (Mar.–Apr., 1973).

Chang, R.W.S., et al., "Predicting Deaths Among Intensive Care Unit Patients" *Crit. Care Med.*, vol. 16, No. 1:34–42 (Jan., 1988).
Gracin, N., et al., "The Use of APACHE II Scores to Select Candidates for Left–Ventricular Assist Device Placement" *J. Heart Lung Transplant*, vol. 17, No. 10:1017–1023 (Oct., 1998).
Higgins, T.L., et al., "ICU Admission Score for Predicting Morbidity and Mortality Risk After Coronary Artery Bypass Grafting" *Ann. Thorac. Surg.*, 64: 1050–1080 (1997).
Knaus, W.A., et al., "APACHE II A Severity of Disease Classification System" *Crit. Care Med.*, vol. 13, No. 10:818–829 (Oct., 1985).
MacGowan, G.A., et al., "Predicting Short–Term Outcome in Severly Ill Heart Failure Patients: Implications Regarding Listing for Urgent Cardiac Transplantation and Patient Selection for Temporary Ventricular Assist Device Support" *J. Cardiac Failure*, vol. 4, No. 3:169–175 (Sep., 1998).

(List continued on next page.)

Primary Examiner—Eric F. Winakur
Assistant Examiner—David J. McCrosky
(74) Attorney, Agent, or Firm—Nutter, McClennen & Fish LLP; Thomas J. Engellenner; Ronald F. Cahill (57) ABSTRACT

A decision analysis method for evaluating patient candidacy for a therapeutic procedure is provided. The method includes predicting, in accordance with a predetermined quantitative predicative scoring system, the probability of an adverse effect on such patient absent such procedure where less than all of data elements used in the scoring system may be available. The method is used to predict a probability of death of a patient within a predetermined period of time and includes predicting, in accordance with a predetermined quantitative predicative scoring system. The probability of death for such patient within the predetermined period of time being determined from medical data elements of the patient where less than all of such medical data elements may be available for use by the scoring system. A method is also provided for generating a scoring system to predict a probability of death of a patient within a predetermined period of time.

41 Claims, 5 Drawing Sheets

OTHER PUBLICATIONS

Niskanen, M., et al., "Acute Physiology and Chronic Health Evaluation (APACHE II) and Glasgow Coma Scores as Predictors of Outcome from Intensive Care After Cardiac Arrest" *Crit. Care Med.,* vol. 19, No. 12:1465–1473 (Dec., 1991).

Nugent, W.C., "Clinical Applications of Risk–Assessment Protocols in the Management of Individual Patients" *Ann. Thorac. Surg.,* 64:S68–72 (1997).

Osler, T.M., et al., "Predicting Survival, Length of Stay, and Cost in the Surgical Intensive Care Unit: APACHE II Versus ICISS" *J. Trauma: Injury, Infection and Critical Care,* vol. 45, No. 2:234–238 (Aug., 1998).

Oz, M.C., et al., "Screening Scale Predicts Patients Successfully Receiving Long–Term Implantable Left Ventricular Assist Devices" *Circulation,* 92[Suppl II]:II–169–II–173 (1995).

Polderman, K.H., "Interobserver Variability in the Use of APACHE II Scores" *The Lancet,* 353:380 (Jan. 30, 1999).

Rogers, J., et al., "Use of Daily Acute Physiology and Chronic Health Evaluation (APACHE) II Scores to Predict Individual Patient Survival Rate" *Crit. Care Med.,* vol. 22, No. 9:1402–1405 (Sep., 1994).

Rutledge, R., et al., "Illness Severity Adjustment for Outcomes Analysis: Validation of the ICISS Methodology in all 821,455 Patients Hospitalized in North Carolina in 1996" *Surgery,* 124:187–196 (1998).

Rutledge, R., et al., "The End of the Injury Severity Score (ISS) and the Trauma and Injury Severity Score (TRISS): ICISS, an International Classification of Diseases, Ninth Revision–Based Prediction Tool, Outperforms Both ISS and TRISS as Predictors of Trauma Patient Survival, Hospital Charges, and Hospital Length of Stay", *J. Trauma: Injury, Infection, and Critical Care,* vol. 44, No. 1:41–49 (Jan., 1998).

Saxon, L.A., et al., "Predicting Death From Progressive Heart Failure Secondary to Ischemic or Idiopath Dilated Cardiomyopathy" *Amer. J. Cardio.,* 72:62–65 (Jul. 1, 1993).

Schafer, J.H., "Outcome Prediction Models on Admission in a Medical Intensive Care Unit: Do They Predict Individual Outcome?" *Crit. Care Medicine,* vol. 18, No. 10:1111–1118 (Oct., 1990).

Van Brommel, E.F.H., et al., "Use of APACHE II Classification to Evaluate Outcome and Response to Therapy in Acute Renal Failure Patients in a Surgical Intensive Care Unit" *Renal Failure,* vol. 17, No. 6:731–742 (1995).

Wagner, D.P., et al., "Daily Prognostic Estimates for Critically Ill Adults in Intensive Care Units: Results from a Prospective, Multicenter, Inception Cohort Analysis" *Crit. Care Med.,* vol. 22, No. 9:1359–1372 (Sep., 1994).

Zimmerman, J.E., et al., "Evaluation of Acute Physiology and Chronic Health Evaluation III Predictions of Hospital Mortality in an Independent Database" *Crit. Care Med.,* vol. 26, No. 8:1317–1326 (1998).

Knaus, Wa et al. "The Apache III Prognostic System. Risk Prediction of Hospital Mortality For Critically Ill Hospitalized Adults" Chest Dec. 1991;100(6):1619–36 Abstract.

* cited by examiner

| PATIENT | MEDICAL DATA — MEDICAL DATA ELEMENTS | | | | | | | | | | | |
|---|---|---|---|---|---|---|---|---|---|---|---|---|
| $n$ | $X_1$ | $X_2$ | $X_3$ | $X_4$ | $X_5$ | $X_6$ | $X_7$ | $X_8$ | ———— | $X_{M-2}$ | $X_{M-1}$ | $X_M$ |
| $n_1$ | ✓ | | | | ✓ | | | | ———— | | ✓ | ✓ |
| $n_2$ | | ✓ | | | | ✓ | | | ———— | | | |
| ⋮ | | | | | | | | | | | | |
| $n_{N1}$ | ✓ | | | | | ✓ | | | ———— | ✓ | | ✓ |
| $n_N$ | | | ✓ | | | | | ✓ | ———— | | ✓ | ✓ |

KEY:
✓ = MEDICAL DATA ELEMENT AVAILABLE DURING FIRST 24 HOURS AFTER PATIENT WAS ADMITTED TO ICU, CCU, CVICU, ETC.

FIG. 2B

| MEDICAL DATA ELEMENT | P-VALUE |
|---|---|
| $X_1$ | $P_{X1}$ |
| $X_2$ | $P_{X2}$ |
| $X_3$ | $P_{X3}$ |
| $X_4$ | $P_{X4}$ |
| $X_M$ | $P_M$ |

| PATIENT | $x_1$ $P_1 > TH_1$ $0 \leq TH_1$ | $x_2$ $P_2 > TH_2$ $0 \leq TH_2$ | --- | $x_M$ $P_n > TH_n$ $0 \leq TH_m$ | TOTAL POINTS GROUP A | TOTAL POINTS GROUP B | TOTAL POINTS GROUP C | PATIENT AGE |
|---|---|---|---|---|---|---|---|---|
| $n_1$ | $P_1 > TH_1$ $0 \leq TH_1$ | $P_2 > TH_2$ $0 \leq TH_2$ | --- | --- | $T_{A1}$ | $T_{B1}$ | $T_{C1}$ | $A_1$ |
| $n_N$ | $P_1 > TH_1$ $0 \leq TH_1$ | $P_2 > TH_2$ $0 \leq TH_2$ | --- | $P_m > TH_m$ | $T_{AN}$ | $T_{BN}$ | $T_{CN}$ | $A_N$ |

DECISION ANALYSIS SYSTEM AND METHOD FOR EVALUATING PATIENT CANDIDACY FOR A THERAPEUTIC PROCEDURE

BACKGROUND OF THE INVENTION

This invention relates generally to decision analysis systems and methods and more particularly to decision analysis systems and methods used for evaluating patient candidacy for a therapeutic procedure. The invention also relates to a method for generating a scoring system to predict a probability of death of a patient within a predetermined period of time.

As is known in the art, patient selection for a therapeutic procedure or facility which may have only limited availability is a difficult task for a physician or health care unit. One system which has been used to assist the physician in assessing the outcome and quality of care in intensive care units (ICUs) is the so-called "Acute Physiology, Age, Chronic Health Evaluation (APACHE) scoring system. See for example, the article entitled "Interobserver variability in the use of APACHE II scores", by Polderman, et al., published in THE LANCET, vol. 353, Jan. 30, 1999, page 380. The APACHE scoring system has also been used in predicting deaths among intensive care unit patients, see "Predicting deaths among intensive care unit patients" by Chang et al. CRITICAL CARE MEDICIAN 1998. Other scoring systems have been used, for example, in predicting morbidity and mortality risk after coronary artery bypass grating, see for example, "ICU Admission Score for Predicting Morbidity and Mortality Risk After Coronary Artery Bypass Grafting" by Higgins et al., The Society of Thoracic Surgeons. 1997 and in predicting patient success after implantation of a Left Ventricle Assist Device (LVAD), see "Screening Scale Predicts Patient Successfully Receiving Long-Term Implantable Left Ventricular Assist Devices", by Oz et al., Supplement II, Circulation, Vol. 92, No. 9. Nov. 1, 1995.

With such scoring systems, a plurality of medical data elements are used to obtain the score. However, all of such elements are required to obtain a valid predictability result. Therefore, such scoring systems are not useful during a life-threatening decision, such as where heart replacement procedure is under consideration, because all of the required medical elements may not be available.

SUMMARY

In accordance with the invention, a decision analysis method for evaluating patient candidacy for a therapeutic procedure is provided. The method includes predicting, in accordance with a predetermined quantitative predicative scoring system, the probability of an adverse effect on such patient absent such procedure where less than all of the medical data elements used in such scoring system may be available.

In one embodiment, the method is used to predict a probability of death of a patient within a predetermined period of time. The method includes predicting, in accordance with a predetermined quantitative predicative scoring system, the probability of death for such patient within the predetermined period of time from medical data elements of the patient where less than all of such medical data elements may be available. Thus, such method is useful for selection of a candidate during a life-threatening interval or moment when all of the medical data elements used in the scoring system might not be available.

In accordance with one embodiment, a decision analysis method for evaluating patient candidacy for a therapeutic procedure is provided. The method includes generating a point total within each of a plurality of groups. Each one of the groups has different ones of a plurality of medical data elements. The method includes determining whether the point total generated for each one of the groups exceeds a predetermined total group threshold. From such determination, the method includes predicting the probability of an adverse effect on such patient absent such procedure.

In accordance with another embodiment of the invention, a method is provided for generating a scoring system to predict a probability of death of a patient within a predetermined period of time. The method includes obtaining medical information comprising a plurality of medical data elements from each one of a plurality of patients. The information includes only those data elements available during a predetermined period of time after such one of the patients has been admitted to a critical care unit. A significance value is determined for each of the medical data elements, such value providing an indication of the significance of such medical data elements on any one of the patients dying within the predetermined period of time. From the determined significance values, a plurality of groups of the medical data elements is established with the medical data elements in each one of the groups having significance values within a corresponding predetermined significance value range. Each medical data element is dichotomized with a corresponding inclusion/exclusion threshold level. A point value is assigned to each one of such dichotomized medical data elements. For each one of the patients, a total of the point values is determined for each one of the groups including in such total only the medical elements determined by the dichotomization to be included within such total. A group threshold level is established for each one of the groups. A binary output is produced for each one of the groups in accordance with a comparison between the total of the points determined for such one of the groups and the corresponding group threshold. The binary outputs from the plurality of groups are processed to provide a score corresponding to each one of the binary outputs, such score indicating a probability of death with the predetermined period of time.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
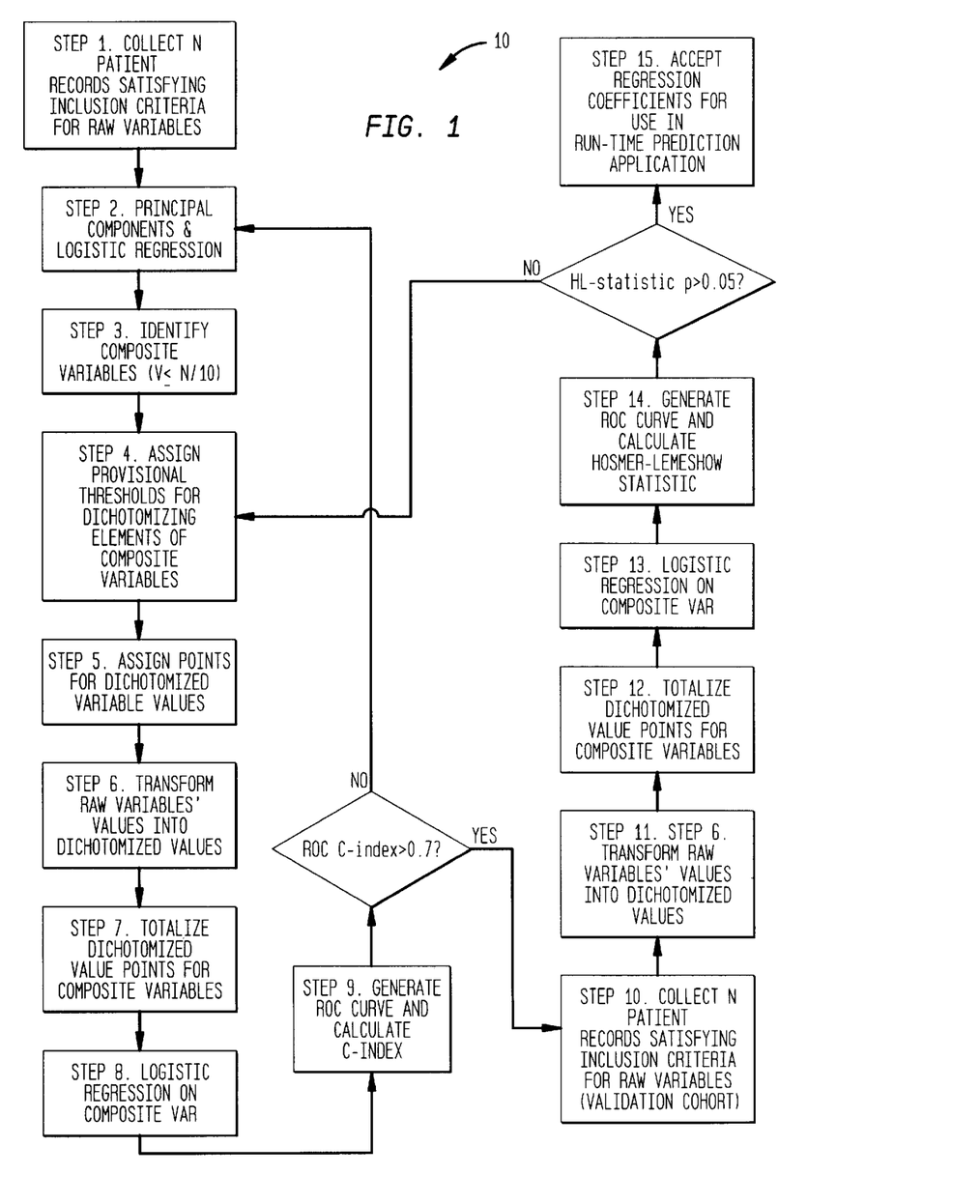
FIG. 1 is a flow diagram of the steps used to generate a scoring system used to predict a probability of death of a patient within a predetermined period of time in accordance with the invention.

Referring now to FIG. 1, a flow diagram 10 is shown of the steps used to generate a scoring system used to evaluate patient candidacy for a therapeutic procedure, here to predict a probability of death of a patient within a predetermined period of time. In Step 1, medical data is collected from a plurality of N, for example 138 patients, having either been scheduled for cardiovascular surgery or cardiology patients within the first 24 hours after such patients were transferred to an intensive, or critical care unit, such as an ICU, CCU, or CVICU. The medical data included elements (i.e., elementary variables) which were typically available from patient medical record. For example, such medical data may include the following data elements: clinical data, hemodynamic data, laboratory data, pharmacy data, radiographic data, echocardiographic data, and electrocardiographic data. Thus, while there might be a variety of elements which a physician may wish to know about the patient, such elements might not be available at such time. A selection is made as to those elements which are most typically available and which are most likely to have an effect on mortality. Here, the following medical data elements, $X_1$–$X_M$ are selected, where here M is 36:

$X_1$ is a 6-min walk test (6MW)—Distance in meters patient is able to walk on a flat surface without stopping, limited by difficulty breathing, chestpain, or other discomfort.

$X_2$ is Acute renal failure (ARF)—Severe decrease in kidney function of recent onset.

$X_3$ is Arterial ketone body ratio (AKBR)—Ratio of concentration of beta-hydroxybutyrate to concentration of acetoacetate in an arterial plasma specimen.

$X_4$ is Arterial pH—The base-10 logarithm of the concentration of H+ in a heparinized arterial blood specimen.

$X_5$ is Automatic implanted cardioverter-defibrillator (AICD)—Patient currently has such a device implanted.

$X_6$ is Body mass index (BMI)—Patient's mass in kilograms, divided by the square of the patient's height in meters.

$X_7$ is Candidate for reoperation in a patient who recently received cardiothoracic surgery (REOP)

$X_8$ Cardiac pacemaker (PACE)—Patient currently has such a device, either implanted or used externally.

$X_9$ is Central venous pressure (CVP)—Pressure in major systemic vein, usually subclavian vein or vena cava, expressed in milliliters mercury.

$X_{10}$ is Continuous positive airway pressure (CPAP)—Type of mechanical ventilation support used to help support patients whose lung function is failing.

$X_{11}$ is Diagnosis of ischemic heart disease (IHD)

$X_{12}$ is Diagnosis of chronic rejection following heart transplantation (REJ)

$X_{13}$ is Electrocardiogram QRS interval (QRS)—Time measured in seconds between the beginning of the "Q" and the end of the "S" portion of the electrocardiogram waveform, corresponding to ventricular contraction.

$X_{14}$ is Glasgow coma scale (GCS)—Standardized fifteen-point scale for assessing level of consciousness and coma.

$X_{15}$ is Intra-aortic balloon pump (IABP) or other mechanical assist—Patient currently has such a device implanted.

$X_{16}$ is Inotrope medications $X_{17}$ is Mean arterial pressure (MAP)

$X_{18}$ is Left ventricular ejection fraction (LVEF)—Average percentage of the volume contained in the left ventricle at end-diastole that is ejected by the end of systole with each stroke.

$X_{19}$ is Left ventricular end-diastolic index (LVEDI)—Ratio of volume in milliliters of the left ventricle chamber measured by arteriography-ventriculography or by echocardiography, divided by the patient's body surface area in meters-squared.

$X_{20}$ is Maximum oxygen consumption (MVO2)—Patient's metabolic oxygen consumption rate under conditions of maximal exercise, in milliliters of oxygen per minute, divided by the patient's mass in kilograms.

$X_{21}$ is Mitral valve regurgitation, Grade 2 or more on angiography or echocardiography (MR)

$X_{22}$ is New York Heart Association heart failure classification, Class IV (NYHA)

$X_{23}$ is Plasma norepinephrine (NE)—Laboratory test measuring the concentration of NE in patient's plasma.

$X_{24}$ is Prothrombin time (PT)—Laboratory test measuring the clotting propensity of the patient's plasma.

$X_{25}$ is Serum tumor necrosis factor alpha (TNFα)—Laboratory test measuring the concentration of TNFα in patient's serum.

$X_{26}$ is Serum aspartate aminotransferase (AST)—Laboratory test measuring the activity in units per liter, of the enzyme aspartate aminotransferase in patient's serum.

$X_{27}$ is Serum creatine kinase (CK)—Laboratory test measuring the activity in units per liter, of the enzyme creatine kinase in patient's serum.

$X_{28}$ is Serum creatinine (CREAT)—Laboratory test measuring the concentration of creatinine in patient's serum.

$X_{29}$ is Serum lactic acid (LACT)—Laboratory test measuring the concentration of lactate in patient's serum.

$X_{30}$ is Serum sodium (NA)—Laboratory test measuring the concentration of Na+ in patient's serum.

$X_{31}$ is Serum uric acid (URIC)—Laboratory test measuring the concentration of uric acid in patient's serum.

$X_{32}$ is Urgent heart replacement—Patient's condition is life-threatening and meets criteria for either Category 1 listing for transplantation or mechanical heart replacement on an urgent basis, within 30 days or less.

$X_{33}$ is Urine output (UO)—Average excretion of urine per hour, determined by measured timed collection.

$X_{34}$ is Venous oxygen partial pressure (PvO2)—Concentration of oxygen in venous blood, expressed as pressure in units of millimeters mercury.

$X_{35}$ is Ventilator (VENT)—Type of mechanical ventilation support used to help support patients whose lung function is failing.

$X_{36}$ is White blood count (WBC)—Number of peripheral blood leukocytes per cubic millimeter, measured by automated instrument or by manual microscopy.

Figure 2A:
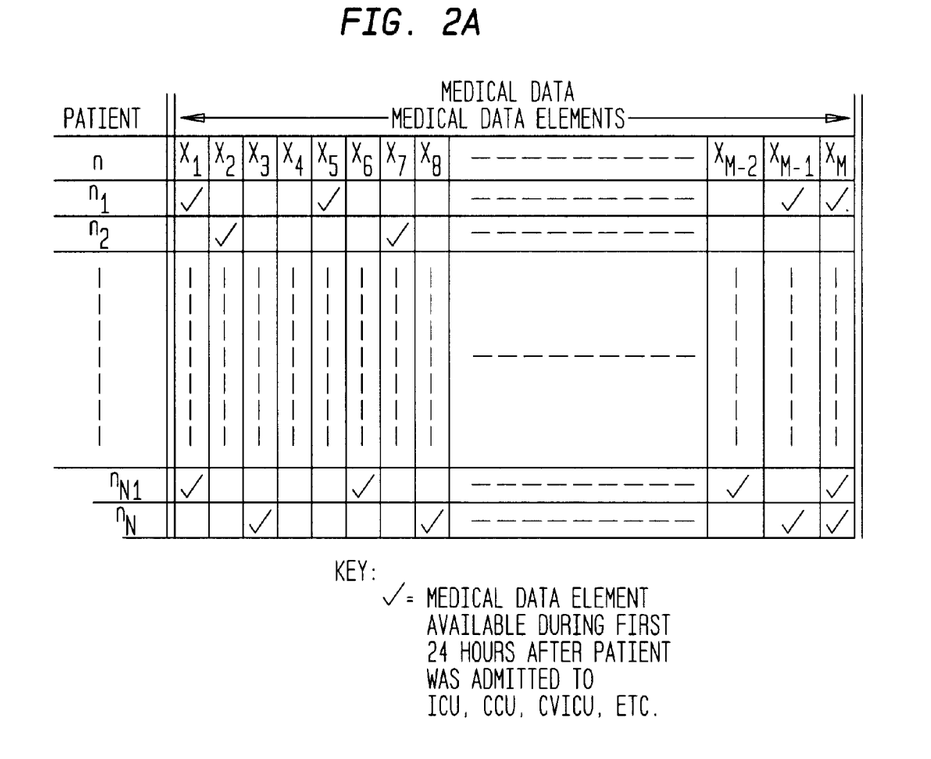
FIGS. 2A–2E are Tables generated at various ones of the steps in the flow diagram of FIG. 1.

The result of Step 1 generates a data base shown in FIG. 2A. It is noted that the availability of the above-mentioned 36 medical data elements for each of the patients is indicated by a check mark (✓). It is noted that for any one of the N patients, one or more of the 36 data elements may not be available.

Figure 2B:
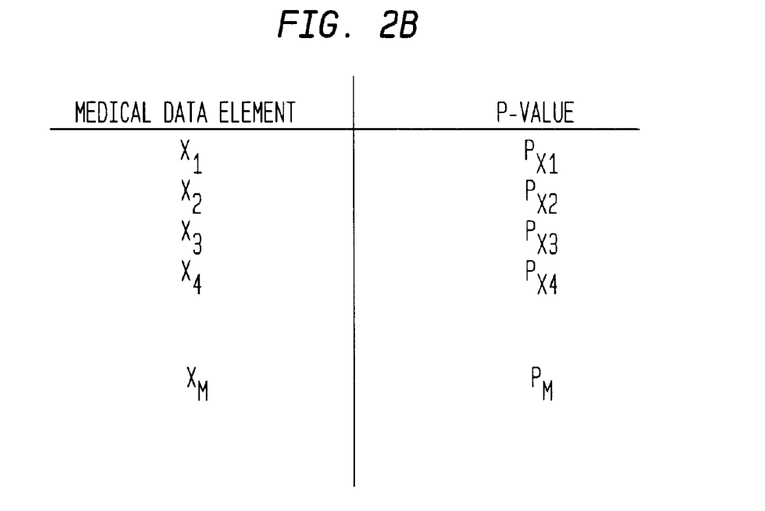

Referring again to FIG. 1, in Step 2, a principal components analysis and logistic regression is performed on the medical data obtained in Step 1 (FIG. 2A). The result of Step 2 produces P values for each of the elements $X_1$–$X_M$, here $X_1$–$X_{36}$, as shown in FIG. 2B. As is known, the P values provide an indication of the degree of significance of such element on a hypothesis being tested, here, in this example, the probability of dying within a predetermined number of days after being transferred to the critical care unit. Thus, in Step 1, the method obtains medical information comprising a plurality of medical data elements from each one of a plurality of patients. As noted above, such information includes only those data elements available within a predetermined period of time after such one of the patients has been transferred to a critical care unit. In Step 2, a determination is made of a significance value, here P value, sometimes referred to as alpha-level, for each of the medical data elements. Such value provides an indication of the significance of such medical data elements on any one of the patients dying within a predetermined number of days from such patient being transferred to the critical care unit.

Referring again to FIG. 1, in Step 3, from the determined significance values, the method establishes a plurality of, V, groups of the medical data elements in such a way that the medical data elements in each one of the groups, have a similar significance level, or here P value. That is, from the determined significance values, a plurality of, here V, groups of the medical data elements is established with the medical data elements in each one of the groups having significance values within a corresponding predetermined significance value range. As will become apparent, each one of the groups is in effect a composite variable. The number of groups, V, is here less than or equal to the number of patients divided by 10, here V is three, indicated in FIG. 2C as Group A, Group B, and Group C. Here, significance values, here the P values, for each of the medical data elements $X_1$–$X_M$, here $X_1$–$X_{36}$, are listed in increasing value, $P_{xi}$–$P_{xj}$ for corresponding data elements $X_1$–$X_j$.

Figure 2C:
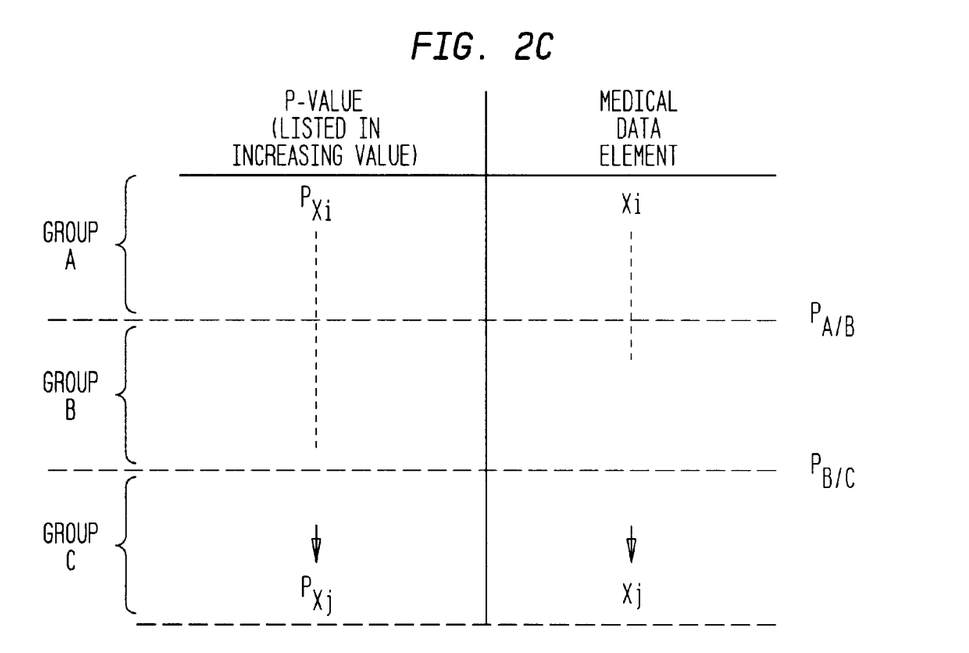

It is noted in FIG. 2C, a significance value threshold level, here a P value, between Group A and Group B (i.e., the boundary indicated by a significance value threshold $P_{A/B}$ in FIG. 2C) is established by examination of the data in FIG. 2C. Here, the significance value threshold $P_{A/B}$ is chosen as 0.02. In like manner, a significance value threshold, here P value, between Group B and Group C (i.e., the boundary indicated by a significance value threshold $P_{A/B}$ in FIG. 2C) is established by examination of the data in FIG. 2C. Here, the significance value threshold $P_{B/C}$ is chosen as 0.10. Thus, from the determined significance values, a plurality of, here three groups of the medical data elements is established, the medical data elements in each one of the groups having significance values within a predetermined significance value threshold. Thus, the following Table was generated:

| GROUP A | GROUP B | GROUP C |
|---|---|---|
| $X_{16}$ | $X_{32}$ | $X_7$ |
|  |  | $X_{11}$ |
| $X_{15}$ | $X_6$ | $X_{12}$ |
| $X_{17}$ | $X_4$ | $X_{20}$ |
| $X_{18}$ | $X_{36}$ | $X_1$ |
| $X_9$ | $X_{35}$ | $X_{13}$ |
| $X_{24}$ | $X_{10}$ | $X_8$ |
| $X_{29}$ | $X_{14}$ |  |
|  |  | $X_5$ |
| $X_{34}$ |  | $X_{19}$ |
| $X_{37}$ |  | $X_{21}$ |
| $X_3$ |  | $X_{22}$ |
| $X_{30}$ |  | $X_{23}$ |
| $X_{33}$ |  | $X_{25}$ |
| $X_{28}$ |  | $X_{26}$ |
| $X_2$ |  | $X_{27}$ |

Referring again to FIG. 1, in Step 4 a data element threshold level TH is provisionally established for each of the data elements. In the process of validating the model, the provisional threshold level TH may be modified as will be described below. Thus, here data element threshold levels $TH_1$–$TH_{36}$ are established for each of the medical data elements $X_1$–$X_{36}$, respectively. As will be described below, these significance value threshold levels may be changed and are thus to be considered at this point is the process as "provisional" significance value thresholds for each of the groups, or composite variables. Thus, in Step 4, a provisional threshold is established to thereby dichotomize the elements. In short, in Step 4 each medical data element $X_1$–$X_{36}$ is dichotomized with a corresponding data element threshold level $TH_1$–$TH_{36}$.

The data element threshold levels $TH_1$–$TH_{36}$ here provisionally established are as follows:

| | | |
|---|---|---|
| $TH_1$ = Can the patient walk less than 200 meters in 6 min | $TH_2$ = Does the patient have acute renal failure | $TH_3$ = Does the patient have an abnormal arterial ketone body ratio |
| $TH_4$ = Does the patient have an arterial pH < 7.3 | $TH_5$ = Does the patient have an AICD | $TH_6$ = Does the patient have a Body Mass Index < 20 kg/m$^2$ |
| $TH_7$ = Is the patient a candidate for re-op | $TH_8$ = Does the patient have a pacer | $TH_9$ = Is the patient's CVP less than 18 mmHg and greater than 10 mmHg |
| $TH_{10}$ = Is the patient receiving continuous positive airway pressure therapy | $TH_{11}$ = Does the patient have ischemic heart disease | $TH_{12}$ = Doe the patient have chronic rejection s/p orthotopic heart transplant |
| $TH_{13}$ = Is the patient's QRS interval > 0.110 sec | $TH_{14}$ = Is the patient's Glasgow Coma Score less than 12 | $TH_{15}$ = Does the patient have one or more mechanical assist devices (LVAD, IABP) |
| $TH_{16}$ = Is the patient receiving more than one inotrope drug | $TH_{17}$ = Does the patient have a mean arterial pressure < 58 mmHg | $TH_{18}$ = Is the patient's LVEF < 16% |
| $TH_{19}$ = Is the patient's LVEDI > 4.0 cm/m$^2$ | $TH_{20}$ = Is the patients MVO2 < 14 mL/kg/min | $TH_{21}$ = Does the patient 4 + mitral regurgitation |
| $TH_{22}$ = has the patient been NYHA Class IV more than 80% of the time during the past 6 months or the anginal equivalent | $TH_{23}$ = Is the patient's Norepinephrine level > 900 ng/L | $TH_{24}$ = Is the patient's prothrombin time less than 25 sec and more than 17 sec |
| $TH_{25}$ = Does the patient have an TNF-alpha level < 50 ng/L | $TH_{26}$ = Is the patient's AST > 320 U/L | $TH_{27}$ = Is the patient's CK > 2000 U/L |
| $TH_{28}$ = Is the patient's creatinine less than 3.0 mg/dL | $TH_{29}$ = Does the patient have an abnormal lactic acid level | $TH_{30}$ = Is the patient's sodium level less than 133 mEq/L |
| $TH_{31}$ = Does the patient have an abnormal uric acid level | $TH_{32}$ = Is in urgent need of heart replacement | $TH_{33}$ = Is the patient's urine output less than 30 mL/hr |
| $TH_{34}$ = Does the patient have an abnormal PVO2 | $TH_{35}$ = Is the patient on a ventilator | $TH_{36}$ = Is the patient's WBC > 17,000 |

Referring again to FIG. 1, in Step 5, a point value is assigned to each one of such medical data elements to be an included data element or an excluded medical data element as determined by the threshold level TH corresponding to such one of the medical data elements. In the present embodiment, all of the point values were set equal to one. It may be that, in other embodiments where a larger number N of patient records is available to develop the model (e.g., ten-fold greater than N in the present embodiment), it will be possible statistically to assign different point values for each one of such medical data elements. In general, different point values will be based on the different variances of the individual medical data elements. For example, a medical data element having a smaller variance would be accorded a higher point value than a medical data element having a larger variance. The process is TABLE I below:

In this example, the following Table I is established:

TABLE I

| GROUP A | GROUP B | GROUP C |
|---|---|---|
| $X_{16}$ { More than one inotrope} = 1 point | $X_{32}$ {Urgent heart replacement} = 1 point | $X_7$ {Re-op candidate} = 1 point |
| $X_{15}$ {IABP or other mechanical assist} = 1 point | $X_6$ {Body Mass Index < 20 kg/m$^2$} = 1 point | $X_{11}$ {Ischemic heart disease} or $X_{12}$ = {chronic rejection s/p HTX} = 1 point |
| $X_{17}$ { Mean Art. Pressure < 58 mmHg} = 1 point | $X_4$ {Arterial pH < 7.30} = 1 point | $X_{20}$ {MVO2 < 14 mL/kg/min}, or $X_1$ {6-min walk < 200 meters} = 1 point |
| $X_{18}$ {LVEF < 16%} = 1 point | $X_{36}$ {WBC > 17,000} = 1 point | |
| $X_9$ {10 < CVP < 18 mmHg} or $X_{24}$ {17 < PT < 25 sec} = 1 point | $X_{35}$ {On ventilator} or $X_{10}$ {CPAP} = 1 point | $X_{13}$ {QRS > -.110 sec}, or $X_8$ {pacer}, or $X_5$ {AICD} = 1 point |
| $X_{29}$ {Abnormal LACT} or $X_{34}$ {PvO2} or $X_{37}$ {URIC} or $X_3$ {AKBR} = 1 point | $X_{14}$ {Glasgow Coma Scale < 12} = 1 point | $X_{19}$ {LVEDI > 4.0 cm/m2}, or $X_{21}$ {4 + MR} = 1 point |
| $X_{30}$ {Sodium < 133 mEq/L} = 1 point | | $X_{22}$ {NYHA Class IV more than 80% of time for past 6 months, or anginal equiv.} = 1 point |
| $X_{33}$ {Urine output < 30 mL/hr} = 1 point | | $X_{23}$ {Norepinephrine level > 900 ng/L} or $X_{25}$ {TNF-alpha > 50 ng/L} = 1 point |
| $X_{28}$ Creatinine > 3.0 mg/dL = 1 point | | |
| $X_2$ {Acute renal failure} = 1 point | | $X_{26}$ {AST > 320 U/L}, or $X_{27}$ {CK > 2000 U/L} = 1 point |
| Group A total points = $T_A$ | Group B total points = $T_B$ | Group C total points = $T_C$ |

Figure 2D:
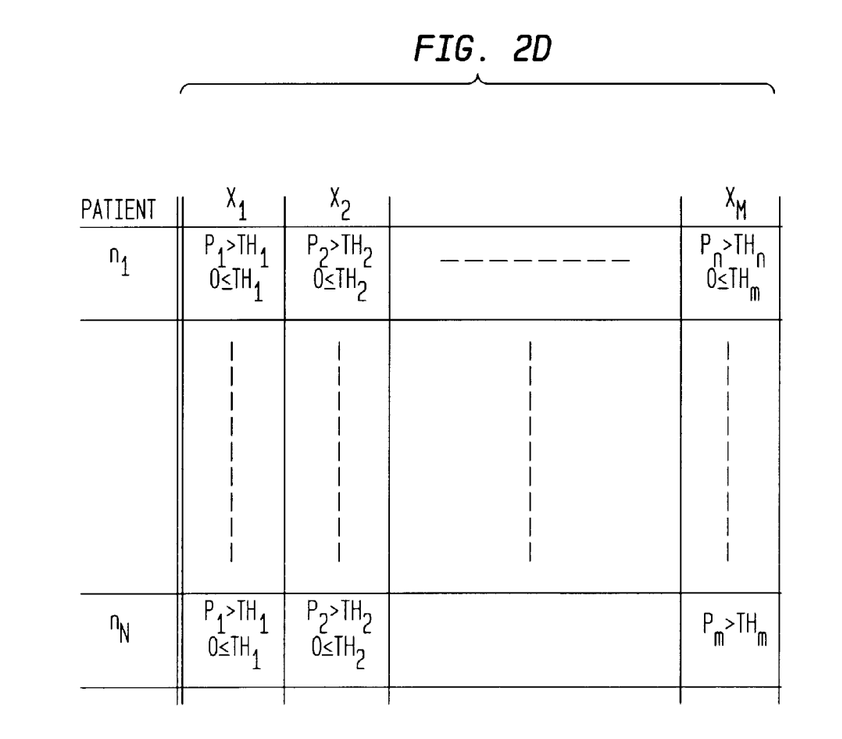

Referring again to FIG. 1, in Step 6, the method transforms the data elements into dichotomized values for each of the here three groups, A, B, and C as shown in FIG. 2D. Thus, for each of the N patients, for each of the data element available for such patient, a determination is made as to whether such element should be included or excluded based on the threshold TH for such element. If such element is available and is to be included, the points assigned to such element are included for such patient.

Thus, a point value is assigned to each one of such medical data elements to be an included data element or an excluded medical data element as determined by the significance value threshold corresponding to such one of the medical data elements.

Figure 2E:
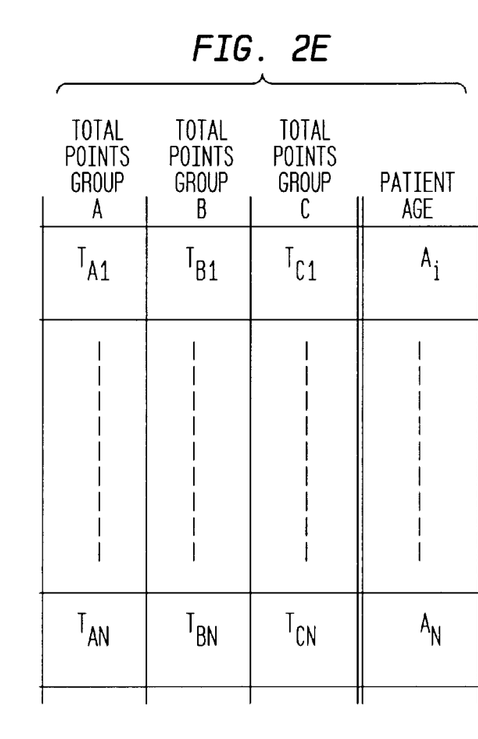

Referring again to FIG. 1, in Step 7, for each one of the N patients, a summation of the point value for each of the here three groups is obtained, as shown in FIG. 2E. Thus, point totals in Groups A, B and C for patients $n_1$–$n_N$ are: $T_{A1}$, $T_{B1}$, $T_{C1}$–$T_{AN}$, $T_{BN}$, $T_{CN}$, respectively as indicated.

It is noted that in FIG. 2E the ages $A_1$–$A_N$ of the N patient are also recorded.

Referring to FIG. 1, in Step 8 a logistic regression is performed on Groups for each one of a plurality of, here 4, age categories. A group threshold level $GTH_A$, $GTH_B$, and $GTH_C$ is established using this logistic regression for each one of the three groups, A, B and C, respectively. Thus, for each one of the age categories, in effect a third "Group" or composite variable, a logistic progression is performed using the total points ($T_{A1}$, $T_{B1}$, $T_{C1}$–$T_{AN}$, $T_{BN}$, $T_{CN}$) in each one of the three Groups A, B and C to determine the percentage of the N patients dying within a predetermined period of time, here thirty days, after being transferred to the critical care unit. Thus, the method determines, for each one of the patients in each of the age categories, an logic, here a yes/no, dichotomized indication, of whether the determined point values in each one the groups exceeds the group threshold level for such one of the groups. Here, in this example, there are for each age category, three logic indications to there provide 16 three bit binary words. Thus, for each one of the patients, a total of the point values is determined for each one of the groups including in such total only the medical elements determined by the dichotomization to be included within such total. A group threshold level is established for each one of the groups. A binary output is produced for each one of the groups in accordance with whether a comparison between the total of the points determined for such one of the groups and the corresponding group threshold. The binary outputs from the plurality of groups are processed to provide a score corresponding to each one of the binary outputs indicating a probability of death with the predetermined period of time.

The binary outputs are then used to establish, for each one of the age categories, the percentage of patients having the same score (i.e., patients which died within the predetermined period of time, here thirty days from being transferred to the critical care unit).

The results of the regression performed in Step 8 here, in this example, produced the following Table II:

TABLE II

| Age Category | $GTH_A \geq 6$? | $GTH_B \geq 4$? | $GTH_C \geq 4$? | Score Prob. of death in < 30 days |
|---|---|---|---|---|
| <46 | No | No | No | <63% |
| | No | No | Yes | 65% |
| | No | Yes | No | 73% |
| | No | Yes | Yes | 75% |
| | Yes | No | No | 77% |
| | Yes | No | Yes | 79% |
| | Yes | Yes | No | 84% |
| | Yes | Yes | Yes | 86% |
| 46–55 | No | No | No | <74% |
| | No | No | Yes | 75% |
| | No | Yes | No | 81% |
| | No | Yes | Yes | 83% |
| | Yes | No | No | 84% |
| | Yes | No | Yes | 86% |
| | Yes | Yes | No | 90% |
| | Yes | Yes | Yes | 91% |
| 56–65 | No | No | No | <81% |
| | No | No | Yes | 83% |
| | No | Yes | No | 88% |
| | No | Yes | Yes | 89% |
| | Yes | No | No | 90% |
| | Yes | No | Yes | 91% |
| | Yes | Yes | No | 93% |
| | Yes | Yes | Yes | 94% |
| 66–75 | No | No | No | <88% |
| | No | No | Yes | 89% |
| | No | Yes | No | 92% |
| | No | Yes | Yes | 93% |
| | Yes | No | No | 93% |
| | Yes | No | Yes | 94% |
| | Yes | Yes | No | 95% |
| | Yes | Yes | Yes | 96% |

Thus, described above is a method for predicting 30-day probability of death due to severe heart failure, and a method for developing a software algorithm to produce this prediction. The inputs to the method and to the software of the present invention are the answers given by a person to a series of measurements, questions, or clinical observations that pertain to clinical and hemodynamic variables. The output of the software algorithm is a predicted mortality probability between 0 and 1 (0%–100%). Such a prognostic scoring technique may serve as a guide to avoid heart replacement in patients who are not sufficiently sick to require it (and who might be helped by conventional therapy, including LVADS), and those who are too sick to be helped despite the implantation of a replacement heart.

An initial model of the above-described method was based on available retrospective cases. The predictive model embodied by the chosen set of mathematical relationships is tested on an entirely different set of patients (validation cohort, Steps 10 through 14, FIG. 1) that were not included in the derivation set. In the embodiment and realization performed by model was verified and based on case records retrieved retrospectively and prospectively. It is noted that the method (FIG. 1) also provides for modification of the Group boundaries $P_{A/B}$, $P_{B/C}$ if the ROC has a C-index>0.70.

The validation cohort consisted of forty-two case records gathered from four clinical centers (Steps 10 through 14, FIG. 1; Step 10 corresponds to Step 1; Step 11 corresponds to Step 6; Step 12 corresponds to Step 7; Step 13 corresponds to Step 8; Step 14 corresponds to Step 9). Each center requested data from their Medical Records Departments. The criteria for record selection were based strictly on ICD-9 codes for heart failure and CPT codes for inadequate hemodynamics refractory to maximal medical therapy for at least 24 hours. Data collected within the first 24-hour period following transfer to the ICU, CCU, CVICU, were used for mortality prediction based on the invention. Patient status, dead or alive, at 30 days was a recorded outcome parameter.

Data for a maximum of 55 variables are collected for each subject. A minimum of 14 available variables from each patient is required for prediction. Four composite variables with age being the only lone variable were derived from logistic regression analysis. Table 1 shows the makeup of the three other composite variables. For example, a total of 15 measurable quantities contribute to the composite variable A. In order to tolerate missing information, a total of 10 parameters are used for model scoring for this composite variable. Similarly, there are 6 scoring parameters and 7 measurable quantities in composite variable B, and 8 and 16 respectively for C. No imputation for missing data is performed at this level. The absence of obvious connection among the parameters in each composite variable points to the complexity of physiology rather than the inadequacy of the model. The use of a comprehensive model, indeed, may serve as an objective tool. Each parameter is assigned one point based on a threshold. A composite variable point score is then derived. The composite variables are further dichotomized as shown in Table III above. The point thresholds for $GTH_A$, $GTH_B$, and $GTH_C$ respectively are set at $GTH_A \geq 6$, $GTH_B \geq 4$, and $GTH_C \geq 4$ for YES and NO otherwise. The Cox Proportional Hazards Regression approach is applied using these 3 variables and Age divided into 4 age categories to arrive at a mortality prediction for each patient with a particular point score.

The age range in the validation cohort was between 20 to 79, with a mean of 54.6±13.6 years old. The male to female ratio was 2.7. The distribution of CHF, CHD, and other Heart problems was 60%, 30%, and 10%. All patients received conventional medical therapy with 38% (16/42) receiving LVAD as a bridge to transplant. Four of the sixteen LVAD patients and twenty-two of the twenty-six medical patients did not survive beyond 30 days. The Kaplan-Meier Survival function for this group of patients is shown in FIG. 1 with LVAD patients censored. The mortality at 30 days is 85%. The overall mortality is 62% including LVAD subjects.

As noted above, a receiver operator characteristic (ROC) curve is generated for the chosen set of mathematical relationships. The ROC curve represents a graphic display of the true positives (sensitivity) plotted against the false positives (1-specificity). The c-index is used to estimate diagnostic accuracy. The c-index is equivalent to the area under the ROC curve. In brief, it is calculated by determining the probability of predicting mortality correctly in every possible pair of patients: one who dies, the other who does not. A bootstrap method was used to calculate directly this measure of accuracy by generating 1000 data sets from a database by random sampling with replacement. Comparisons between the c-index for the method described above and prior art models (e.g., APACHE) were assessed based on the confidence. Statistical significance was accepted at the 5% level. It is noted that the method (FIG. 1) also provides for modification of the dichotomization thresholds and/or Group boundaries $P_{A/B}$, $P_{B/C}$ if the validation dataset has a HL-statistic$\leq$0.05.

The results of the above described method and the predictive ability of the method according to the invention, are described below, and the description which follows further illustrates the methods described above. There were no significant differences in age, gender ratio, body mass index or neck circumference of patients of the derivation data set compared with the validation data set.

Figure 3:
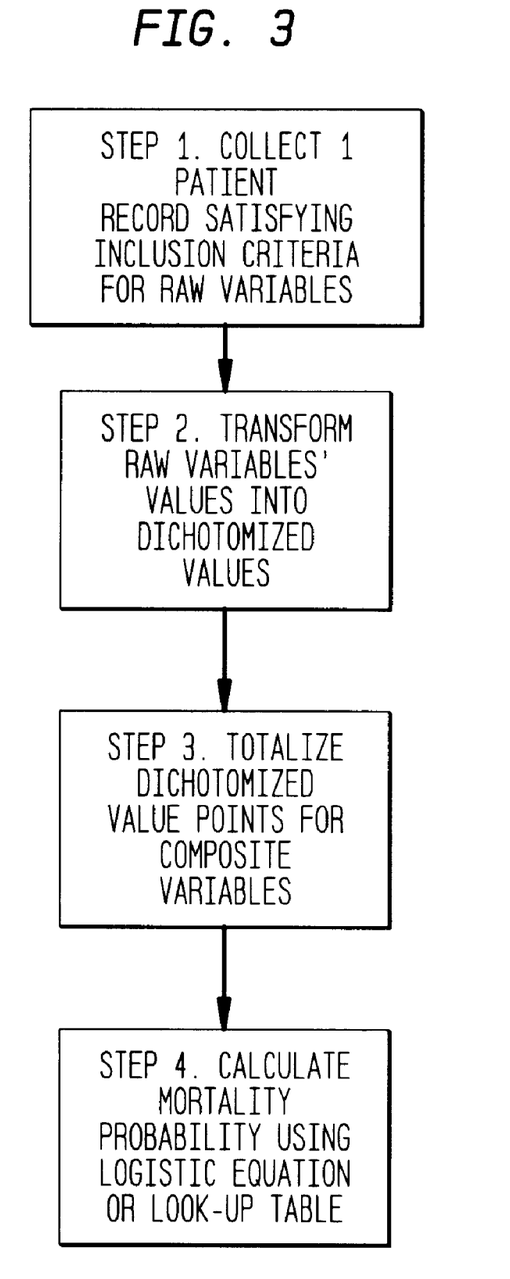
FIG. 3 is a flow diagram of steps used to evaluate patient candidacy for a therapeutic procedure, in this embodiment heart replacement using a probability of death of the patient within a predetermined period of time.

Having established the Tables I and II, the physician can use Table II to determine the suitability of the patient, i.e., candidate, for the therapeutic procedure, here a replacement heart. Thus, referring to FIG. 3, the physician collects all of the elements $X_1$–$X_{36}$ which are available. The obtained variables are then transformed into dichotomized values using the thresholds, TH, described above in connection with Table I. The values in each one of the three Groups, A, B and C are totaled in accordance with Table II. The total in each of the Groups A, B and C is compared with the Group thresholds $GTH_A$, $GTH_B$, and $GTH_C$, respectively, to obtain for each one of the three Groups A, B and C a yes or a no answer (i.e., a dichotomized or logical output). That is, does the total in Group A exceed $GTH_A$? Does the does total in Group B exceed $GTH_B$? Does the does total in Group C exceed $GTH_C$? Thus, for each candidate there are three binary (yes or no) answers (i.e., 8 possible indicia for each candidates as shown in Table II. Using the look-up Table II, the mortality of the candidate is determined (i.e., the probability of such candidate living beyond 30 days without a heart replacement).

As will be recognized by one skilled in the art, the present invention is a method, in the form of a score, which takes into account nonlinear relationships and intricate interrelationships among attributes of a complex process. The present inventions also presents a method for developing a score which results in a prediction having more specificity and better calibration than prior art prediction rules developed through traditional regression analysis. It is therefore apparent that the present invention accomplishes the intended objects described above.

The prognostic accuracy of the composite-variable model according to the invention, in the development cohort was superior to that of traditional logistic regression models (ROC areas 86% vs 71%), and its calibration was better. Traditional logistic regression such as APACHE overestimated event rates in this group of high-risk patients (predicted event rate, 95%; observed rate, 85%; N=138, p<0.01). On the validation set of 42 patients, the method according to the invention had ROC areas similar to those of logistic regression (79% vs 68%), but logistic regression again overestimated event rates for a group of high-risk patients. The calibration difference was reflected in the Hosmer-Lemeshow chi-square statistic (13.5, df=8, p<0.10 for the invention; vs. 25.4, df=15, p<0.01 for APACHE, N=42). It is noted in FIG. 1 that if the Hosmer-Lemeshow chi-square statistic p>0.05, the model enables a re-evaluation of the provisionally assigned thresholds for the Groups A, B and C provisionally assigned in Step 4. The method according to the invention has been found accurately estimated 30-day risk of mortality with better calibration than comparable logistic regression models.

The overall predicted mortality in the validation cohort using the invention is 79%±11%. For LVAD subjects only, the predicted mortality had they not been placed on the device is 73%±10%. With LVAD therapy, the 30-day mortality dropped to 27%, an anticipated improved outcome. Similarly, the predicted mortality for the medically managed subjects is 83%±11%. This compares quite favorably with the observed mortality of 85% for this group. For this more seriously ill group, one might expect that heart replacement could be the only chance for survival for some of these patients. Two by two contingency tables were set up to determine whether the invention can be used to differentiate those that should receive conventional therapy including LVAD, versus those that may be helped by heart replacement. A near optimal threshold was determined to be a predicted mortality of 82%. The accuracy of prediction is 79% derived from ROC (receiver operator characteristics). The Table III below shows the 2×2 table for prediction of survival and death with a p-value of <0.02 for a predicted mortality threshold of 82%.

TABLE III

Contingency Table for All Patients

|  | ≧0.82 | <0.82 |  |
| --- | --- | --- | --- |
| Died | 15 | 11 | Sensitivity = 58% |
| Survived | 2 | 14 | Specificity = 88% |
|  | PPV = 88% | NPV = 56% |  |

P < 0.02 where PPV is positive predictive value.

Similar considerations for only the medically treated patients (Table IV below) excluding the LVAD subjects, resulted in a p-value for mortality discrimination of <0.05 at the same predicted mortality threshold of 82%.

TABLE IV

Contingency Table for Medically Treated Patients

|  | ≧0.82 | <0.82 |  |
| --- | --- | --- | --- |
| Died | 14 | 7 | Sensitivity = 67% |
| Survived | 0 | 5 | Specificity = 100% |
|  | PPV = 100% | NPV = 42% |  |

P < 0.05

With a positive predictive value (PPV) for death of 100%, this predicted mortality threshold of 82% would generally insure that only patients with high probability of death would be considered for heart replacement. The negative predictive value (NPV) of 42% suggests that for those patients not considered for heart replacement, nearly half of them can survive without support. This patient group should probably not be considered for heart replacement.

Using this threshold of 82% for subdividing the patients, TABLE IV shows the actual mortality rate of the two divided groups based on the 82% threshold calculated from the invention for the entire cohort including LVAD support and the medical treated patients excluding LVAD support. It is evident that the actual mortality rate for patients in the ≧82% predicted mortality is nearly twice that for subjects in the <82% group. Above this threshold, only 18% of the patients were treated by LVAD compared with 48% of subjects treated with LVAD below this threshold. This difference in treatment provided reflects the severity of the medical conditions of the two patient categories differentiated by the invention. LVADs are implanted in less severely ill patients in this cohort based on current medical practice judgement. This discrimination offered by the invention can be a guide for identifying patients suitable for heart replacement.

Thus, from the above, a decision analysis method has been described for evaluating patient candidacy for a therapeutic procedure, here, in this example, heart replacement procedure. The method predicts, in accordance with a predetermined quantitative predicative scoring system, the probability of an adverse effect on such patient absent such procedure where less than all of such data elements may be available for the such scoring system.

More particularly, in the embodiment described above, a method is provided for predicting a probability of death of a patient within a predetermined period of time. The method includes predicting, in accordance with a predetermined quantitative predictive scoring system, the probability of death for such patient within the predetermined period of time from medical data elements of the patient where less than all of such medical data elements may be available for use by the scoring system.

Still more particularly, the method predicts a probability of death of a patient within a predetermined period of time by generating a point total within each of a plurality of sets of different ones of a plurality of medical data elements where less than all of such data elements may be available; determining whether the point total generated for each one of the sets exceeds a predetermined point total threshold established for each one of the plurality of sets; and from such determination, predicting the probability of death for such patient within the predetermined period of time.

A number of embodiments of the invention have been described. For example, while described for heart replacement, the method may be used to assess the candidacy of a patient for other therapeutic procedures, such as, for example, an LVAD. Nevertheless, it will be understood that various modifications may be made without departing from the spirit and scope of the invention. Accordingly, other embodiments are within the scope of the following claims.

What is claimed is:

1. A method for predicting a healthcare outcome for a patient, comprising:
   (a) collecting data values representing a plurality of medical data elements from a plurality of past patients, the medical data elements being likely to be predictors for the healthcare outcome;
   (b) grouping the medical data elements into a plurality of composite variables, each composite variable including a plurality of medical data elements;
   (c) dichotomizing the medical data elements based on threshold values and assigning points to each medical data element based on the dichotomization;

(d) totaling the dichotomized points within each composite variable for each past patient;

(e) correlating composite variable point totals to healthcare outcome for each past patient to establish a predictive model for the healthcare outcome;

(f) applying the predictive model to the patient to predict the healthcare outcome for the patient.

2. The method of claim 1, wherein the plurality of composite variables comprises at least three composite variables.

3. The method of claim 2, wherein, in addition to at least three composite variables, patient age is collected and maintained as a separate medical data element.

4. The method of claim 1, wherein the medical data elements are grouped into composite variables after determining a significance value for each medical data element, wherein the significance value indicates the significance of the medical data element to the healthcare outcome being predicted, and the plurality of groups each include a plurality of medical data elements having similar significance values.

5. The method of claim 1, wherein the composite variables are dichotomized based on threshold values.

6. The method of claim 5, wherein the composite variables are dichotomized into binary form.

7. The method of claim 1, wherein the medical data elements include only data elements that are available during a predetermined period of time after a patient has been admitted to a clinical care unit.

8. The method of claim 7, wherein the time period is 24 hours.

9. The method of claim 1, wherein the healthcare outcome predicted is mortality within a specified period of time.

10. The method of claim 9, wherein the specified period of time is 30 days.

11. The method of claim 9, wherein the healthcare outcome predicted is mortality without any therapeutic procedure.

12. The method of claim 9, wherein the healthcare outcome predicted is mortality where given a specific therapeutic procedure.

13. The method of claim 12, wherein the predictive model is applied to predict mortality with and without a specific therapeutic procedure for determining whether the specific therapeutic procedure will be effective.

14. The method of claim 13, wherein the predictive model is applied to determine whether the patient is a candidate for a more invasive treatment than the specific therapeutic treatment.

15. The method of claim 14, wherein the more invasive treatment is the implantation of an artificial heart.

16. The method of claim 12, wherein the specific therapeutic procedure is the application of a ventricular assist device.

17. The method of claim 1, further comprising validating the predictive model before applying it to a patient to predict a healthcare outcome.

18. The method of claim 17, wherein validating the predictive model comprises applying the predictive model to a validation cohort of past patients and comparing healthcare outcomes predicted by the predictive model to historical healthcare outcomes.

19. The method of claim 18, wherein the comparison is made by calculating a c-index value.

20. The method of claim 18, further comprising revising threshold values in the predictive model to improve its predictive accuracy.

21. The method of claim 1, wherein the model can be accurately applied to a patient to predict a healthcare outcome where data values are not available for the patient for each of the plurality of medical data elements.

22. The method of claim 21, wherein each composite variable includes a plurality of medical data elements for which data values are available.

23. A method for developing a predictive model for determining a healthcare outcome for a patient, the predictive model operating on a plurality of medical data elements and being capable of predicting a healthcare outcome for the patient when data values for less than all of the plurality of medical data elements are available, the method comprising:

(a) collecting historical patient data values for the plurality of medical data elements;

(b) transforming the data values into dichotomized values;

(c) total the dichotomized values into a plurality of composite variable values; and (d) correlating the composite variable values to historical healthcare outcomes so that the predictive model can predict a healthcare outcome when data values are not available for all of the medical data elements.

24. The method of claim 23, wherein the plurality of composite variables comprises at least three composite variables.

25. The method of claim 24, wherein, in addition to at least three composite variables, patient age is collected and maintained as a separate medical data element.

26. The method of claim 25, wherein the composite variables are dichotomized into binary form.

27. The method of claim 23, wherein the dichotomized values are totaled into a plurality of composite variables by grouping the medical data elements into composite variables after determining a significance value for each medical data element, wherein the significance value indicates the significance of the medical data element to the healthcare outcome being predicted, and the plurality of groups each include a plurality of medical data elements having similar significance values.

28. The method of claim 23, wherein the data values are transformed into dichotomized values based on threshold values established for the medical data elements.

29. The method of claim 23, wherein the composite variables are dichotomized based on threshold values.

30. The method of claim 23, wherein the medical data elements include only data elements that are available during a predetermined period of time after a patient has been admitted to a clinical care unit.

31. The method of claim 30, wherein the time period is 24 hours.

32. The method of claim 23, wherein the healthcare outcome predicted is mortality within a specified period of time.

33. The method of claim 32, wherein the specified period of time is 30 days.

34. The method of claim 32, wherein the healthcare outcome predicted is mortality without any therapeutic procedure.

35. The method of claim 32, wherein the healthcare outcome predicted is mortality where given a specific therapeutic procedure.

36. The method of claim 35, wherein the specific therapeutic procedure is the application of a ventricular assist device.

37. The method of claim 23, further comprising validating the predictive model before applying it to a patient to predict a healthcare outcome.

38. The method of claim 37, wherein validating the predictive model comprises applying the predictive model to a validation cohort of past patients and comparing healthcare outcomes predicted by the predictive model to historical healthcare outcomes.

39. The method of claim 38, wherein the comparison is made by calculating a c-index value.

40. The method of claim 38, further comprising revising threshold values in the predictive model to improve its predictive accuracy.

41. A method for generating a scoring system to predict a probability of death of a patient within a predetermined period of time, comprising:

obtaining medical information comprising a plurality of medical data elements from each one of a plurality of patients, the medical information including only those data elements available during a predetermined period of time after each of the patients has been admitted to a critical care unit;

determining a significance value for each of the medical data elements, the significance value providing an indication of the significance of the medical data elements on any one of the patients dying within the predetermined period of time;

establishing from the determined significance values a plurality of groups of the medical data elements, the medical data elements in each one of the groups having significance values within a corresponding predetermined significance value range;

dichotomizing each medical data element with a corresponding inclusion/exclusion threshold level;

assigning a point value to each one of the dichotomized medical data elements;

for each one of the patients, calculating a total of the point values for each one of the groups including in the total only the medical elements determined by the last-mentioned dichotomization to be included within the total;

establishing a group threshold level for each one of the groups;

producing a binary output for each one of the groups in accordance with a comparison between the total of the points determined for each one of the groups and the corresponding group threshold; and processing the binary outputs from the plurality of groups to provide a score corresponding to each one of the binary outputs indicating a probability of death within the predetermined period of time.

* * * * *

UNITED STATES PATENT AND TRADEMARK OFFICE
CERTIFICATE OF CORRECTION

PATENT NO.    : 6,533,724 B2
DATED         : March 18, 2003
INVENTOR(S)   : Douglas S. McNair It is certified that error appears in the above-identified patent and that said Letters Patent is hereby corrected as shown below:

Title page,
Item [56], References Cited, OTHER PUBLICATIONS, "Van Brommel" should read -- van Bommel --;

Drawings,
Figure 2A, in column PATIENT "$n_{N1}$" should read -- $n_{N-1}$ --;
Figure 2D, in column $X_M$, for PATIENT $n_1$, "$P_n > TH_n$" should read -- $P_m > TH_m$
                                                    $0 \leq TH_m$                    $0 \leq TH_m$ --
Figure 2D, in column $X_M$, for PATIENT $n_N$, "$P_m > TH_m$" should read -- $P_m > TH_m$
                                                                              $0 \leq TH_m$ --

Column 5,
Line 33, "$X_l - X_j$" should read -- $X_i - X_j$ --;

Signed and Sealed this

Eighteenth Day of November, 2003

JAMES E. ROGAN
*Director of the United States Patent and Trademark Office*